(12) United States Patent
Temple

(10) Patent No.: US 10,220,058 B2
(45) Date of Patent: Mar. 5, 2019

(54) SPINAL DISC REGENERATIVE COMPOSITION AND METHOD OF MANUFACTURE AND USE

(71) Applicant: Vivex Biomedical Inc., Atlanta, GA (US)

(72) Inventor: Harry Thomas Temple, Miami, FL (US)

(73) Assignee: Vivex Biomedical, Inc., Atlanta, GA (US)

( * ) Notice: Subject to any disclaimer, the term of this patent is extended or adjusted under 35 U.S.C. 154(b) by 0 days.

(21) Appl. No.: 15/474,450

(22) Filed: Mar. 30, 2017

(65) Prior Publication Data
US 2017/0202884 A1    Jul. 20, 2017

Related U.S. Application Data

(60) Continuation of application No. 14/697,790, filed on Apr. 28, 2015, now Pat. No. 9,655,929, which is a division of application No. 14/334,318, filed on Jul. 17, 2014, now Pat. No. 10,064,896.

(51) Int. Cl.

| | |
|---|---|
| *A61K 35/32* | (2015.01) |
| *A61B 17/70* | (2006.01) |
| *A61B 17/88* | (2006.01) |
| *A61L 24/00* | (2006.01) |
| *A61L 24/10* | (2006.01) |
| *A61F 2/44* | (2006.01) |
| *A61K 9/19* | (2006.01) |
| *A61L 27/36* | (2006.01) |
| *A61L 27/54* | (2006.01) |
| *A61K 9/00* | (2006.01) |
| *A61K 45/06* | (2006.01) |
| *A61B 17/56* | (2006.01) |

(52) U.S. Cl.
CPC .......... *A61K 35/32* (2013.01); *A61B 17/7061* (2013.01); *A61B 17/8805* (2013.01); *A61F 2/442* (2013.01); *A61K 9/0019* (2013.01); *A61K 9/0085* (2013.01); *A61K 9/19* (2013.01); *A61K 45/06* (2013.01); *A61L 24/0015* (2013.01); *A61L 24/106* (2013.01); *A61L 27/3612* (2013.01); *A61L 27/3658* (2013.01); *A61L 27/54* (2013.01); *A61B 2017/564* (2013.01); *A61F 2002/4435* (2013.01); *A61L 2300/418* (2013.01); *A61L 2400/06* (2013.01); *A61L 2430/24* (2013.01)

(58) Field of Classification Search
None
See application file for complete search history.

(56) References Cited

U.S. PATENT DOCUMENTS

| | | | |
|---|---|---|---|
| 7,713,303 | B2 | 5/2010 | Trieu et al. |
| 8,629,122 | B2 | 1/2014 | Takahashi et al. |
| 2003/0069639 | A1 | 4/2003 | Sander et al. |
| 2004/0068268 | A1 | 4/2004 | Boyd et al. |
| 2007/0003525 | A1 | 1/2007 | Moehlenbruck et al. |
| 2008/0014179 | A1 | 1/2008 | Ferree et al. |
| 2013/0078222 | A1 | 3/2013 | Sakai et al. |
| 2013/0338792 | A1* | 12/2013 | Schmieding ........ A61F 2/30756 623/23.73 |

OTHER PUBLICATIONS

Sigma-Aldrich, "Syringe Needle Gauge Chart".

* cited by examiner

*Primary Examiner* — Allison M Fox
(74) *Attorney, Agent, or Firm* — David L. King

(57) ABSTRACT

The present invention provides a novel way to replenish the disc using retooled disc compositions to repair degenerative discs. There is no better source of proteoglycans than the actual disc material (6) itself. To this end, there has been developed a technique to remove the nucleus pulposus and retool the morphology of the nucleus pulposus to create a powder material (10) that is dry and can be stored at room temperature for long periods of time. This powder (10) can then be reconstituted with a variety of fluids, the most suitable being normal saline or lactated ringers to form a flowable mixture (20).

5 Claims, 3 Drawing Sheets

SPINAL DISC REGENERATIVE COMPOSITION AND METHOD OF MANUFACTURE AND USE

RELATED APPLICATIONS

The present invention is a continuation of co-pending U.S. application Ser. No. 14/697,790 filed on Apr. 28, 2015 entitled "Spinal Disc Regenerative Composition And Method Of Manufacture And Use".

TECHNICAL FIELD

The present invention relates to a spinal disc regenerative composition and method of manufacture and use.

BACKGROUND OF THE INVENTION

Intervertebral discs are soft and compressible. They are interposed between adjacent vertebral body elements of the spine. They act as shock absorbers for the spine, allowing it to flex, bend, and rotate. Degenerative disc disease can occur throughout the spine, but most often occurs in the discs in the lower back (lumbar region) and the neck (cervical region).

As the process of degeneration continues, micro tears or cracks occur in the outer layer (annulus fibrosus) of the disc. The jellylike material inside the disc (nucleus pulposus) may be forced out through the tears or cracks in the annulus, which causes the disc to bulge, break open (rupture), or break into fragments.

The economic impact of degenerative disc disease is enormous accounting for a significant morbidity and lost wages.

The physical properties of the disc are the nucleus pulposus which is composed of type II collagen and the annulus fibrosis which surrounds the disc and gives it significant form. The annulus composed of type I collagen. The nucleus pulposus is largely made up of molecules called proteoglycans. These proteoglycans have an affinity for water. It is this retention of water and the stoichiometry of folded molecules that is responsible for the unique mechanical properties of the disc. If these proteoglycans are depleted, the discs become more rigid and the loss of fluid results in a disc that is thinner and less compliant. Clinically this results in narrowing of the distances between the vertebral elements. This is best seen on magnetic resonance imaging. Typically discs have a bright signal on T2 pulse-weighted sequences and they are hypointense on corresponding T1 images. This is due to the high fluid content of the discs. As the disc loses fluid i.e. the loss of proteoglycans, the disc loses its water signal and becomes anhidrotic and eventually mineralizes. As a result, these individuals develop the symptoms in the spine contributable to loss of the normal disc architecture. As the process of degeneration continues, one develops micro tears or cracks and fissures in the annulus fibrosis and through these cracks and fissures the nucleus pulposus, which is largely gelatinous, may extrude. The extruded disc material may efface the dura and cause significant nerve compression which may result in traumatic neuritic pain and or motor loss. Therefore, once these early changes in disc degeneration are recognized, it may be prudent to replenish the disc with proteoglycans. Currently, synthetic and artificial substitutes are used to stimulate repair.

SUMMARY OF THE INVENTION

The present invention provides a novel way to replenish the disc. These novel disc compositions may be used to repair degenerative discs. There is no better source of proteoglycans than the actual disc material itself. To this end, a technique has been developed to remove the nucleus pulposus and retool the morphology of the nucleus pulposus to create a powder material that is dry and can be stored at room temperature for long periods of time. This powder can then be reconstituted with a variety of fluids, the most suitable being normal saline or lactated ringers solution to form a flowable mixture.

The powder could also be mixed with stem cells that are derived from marrow, fat, blood, or any other source, even the interspinous ligaments. It could be combined with micronized amnion, platelet-rich plasma, and a variety of growth factors that can be encapsulated into pharmacologically active microspheres otherwise known as PAMS. The powder could also be combined with genetically altered cells that produce large amounts of glycosaminoglycans, collagen Type 1 or glucose to form the flowable mixture. The micronized material when rehydrated has a high viscosity and allows the rehydrated material to be flowable as injectable through a cannula. This allows the rehydrated material to be stored in a syringe or other injectable device for insertion into a damaged disc to be treated.

This flowable mixture forms a composite composition between the micronized nucleus pulposus that can then be injected using a syringe or any suitable injection delivery device through a very small cannula as small as 2 mm into the disc space. This instrument can be inserted percutaneously into the disc itself during the process of discography. The flowable material of this composite composition is of a sufficiently high viscosity that once hydrated will not necessarily leak out through the injection portal or through pre-existing cracks and fissures in the annulus fibrosus. If however these cracks and fissures are substantial, they could be sealed with fibrin glue as part of the procedure of introducing the composites.

DEFINITIONS

As used herein and in the claims:

"Cryomill"—The CryoMill is tailored for cryogenic grinding. The grinding jar is continually cooled with liquid nitrogen from the integrated cooling system before and during the grinding process. Thus the sample is embrittled and the chemical composition is preserved. The liquid nitrogen circulates through the system and is continually replenished from an Autofill system in the exact amount which is required to keep the temperature at −196° C. Powerful impact ball milling results in a perfect grinding efficiency. The Autofill system avoids direct contact with LN2 and makes the operation very safe. Its versatility (cryogenic, wet and dry grinding at room temperature) makes the CryoMill the ideal grinder for quantities up to 20 ml. The grinding jar of the CryoMill performs radial oscillations in a horizontal position. The inertia of the grinding balls causes them to impact with high energy on the sample material at the rounded ends of the grinding jar and pulverize it. The grinding jar is continually cooled with liquid nitrogen from the integrated cooling system before and during the grinding process.

"Disc Desiccation"—Disc desiccation is an extremely common degenerative change of intervertebral discs. The incidence climbs with age, and to a large degree a gradual desiccation is a 'normal' part of disc aging. It results from replacement of the hydrophilic glycosaminoglycans within the nucleus pulposus with fibrocartilage.

"Freeze Drying"—Freeze-drying, also known as lyophilisation, lyophilization, or cryodesiccation, is a dehydration process typically used to preserve a perishable material or make the material more convenient for transport and stable at room temperatures in an appropriate contained or package. Freeze-drying works by freezing the material and then reducing the surrounding pressure to allow the frozen water in the material to sublimate directly from the solid phase to the gas phase.

"Hypothermic Dehydration"—hypothermic dehydration depends on placing the object at reduced temperatures above freezing point into a high vacuum chamber allowing it to dry to a desired residual moisture level. The result is dried tissue without fissures, microscopic ice crystal distortion and collapse phenomenon.

"Nucleus Pulposus"—Nucleus pulposus is the gel-like substance in the middle of the spinal disc. It is the remnant of the notochord. It functions to distribute hydraulic pressure in all directions within each disc under compressive loads. The nucleus pulposus consists of large vacuolated notochord cells, small chondrocyte-like cells, collagen fibrils, and proteoglycan aggrecans that aggregate through hyaluronic chains. Attached to each aggrecan molecule are the glycosaminoglycan (GAG) chains of chondroitin sulfate and keratan sulfate. Aggrecan is negatively charged, allowing the nucleus pulposus to attract water molecules. The amount of water and glycosaminoglycans decreases with age and degeneration.

"Proteoglycans"—Proteoglycans are proteins that are heavily glycosylated. The basic proteoglycan unit consists of a "core protein" with one or more covalently attached glycosaminoglycan (GAG) chain(s). The point of attachment is a Ser residue to which the glycosaminoglycan is joined through a tetrasaccharide bridge (e.g. chondroitin sulfate-GlcA-Gal-Gal-Xyl-PROTEIN). The Ser residue is generally in the sequence -Ser-Gly-X-Gly- (where X can be any amino acid residue, but Proline), although not every protein with this sequence has an attached glycosaminoglycan. The chains are long, linear carbohydrate polymers that are negatively charged under physiological conditions, due to the occurrence of sulfate and uronic acid groups. Proteoglycans occur in the connective tissue. Proteoglycans are a major component of the animal extracellular matrix, the "filler" substance existing between cells in an organism. Here they form large complexes, both to other proteoglycans, to hyaluronan and to fibrous matrix proteins (such as collagen). They are also involved in binding cations (such as sodium, potassium and calcium) and water, and also regulating the movement of molecules through the matrix. Evidence also shows they can affect the activity and stability of proteins and signaling molecules within the matrix. Individual functions of proteoglycans can be attributed to either the protein core or the attached GAG chain and serve as lubricants.

BRIEF DESCRIPTION OF THE DRAWINGS

The invention will be described by way of example and with reference to the accompanying drawings in which.

DETAILED DESCRIPTION OF THE INVENTION

Figure 1A:
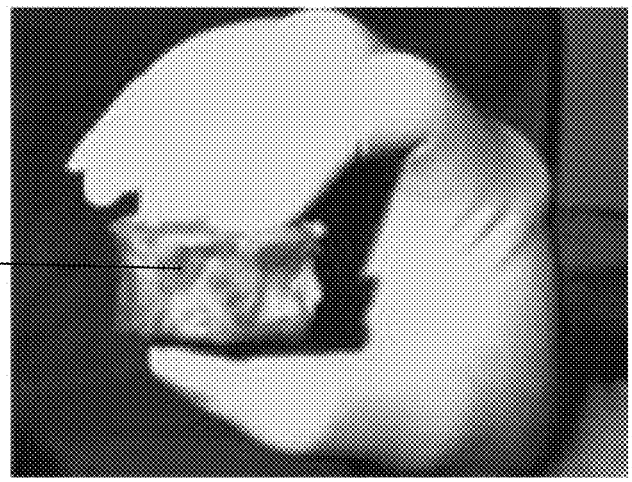
FIG. 1A is a photo of a spinal segment after being cut from a spine segment.
Figure 1B:
FIG. 1B is a photo of a vertebral spine segment wherein the adjacent vertebrae are cut, separated and the disc material removed.
Figure 2:
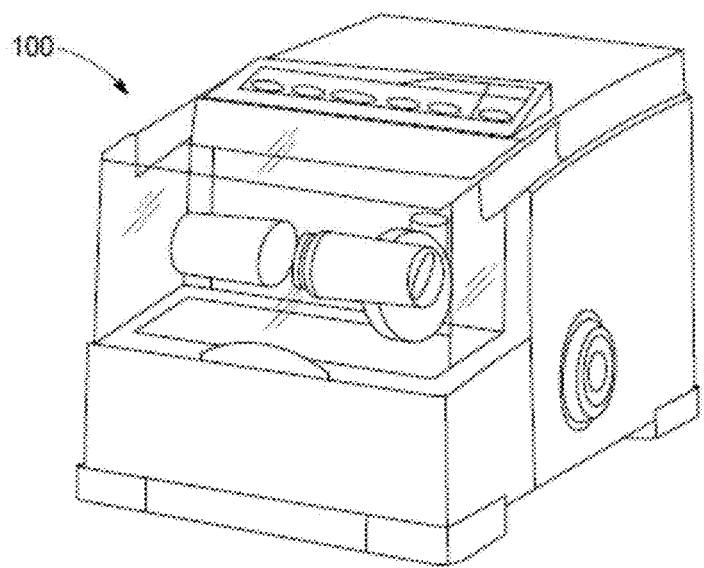
FIG. 2 is a photo of an exemplary cryomill.
Figure 3:
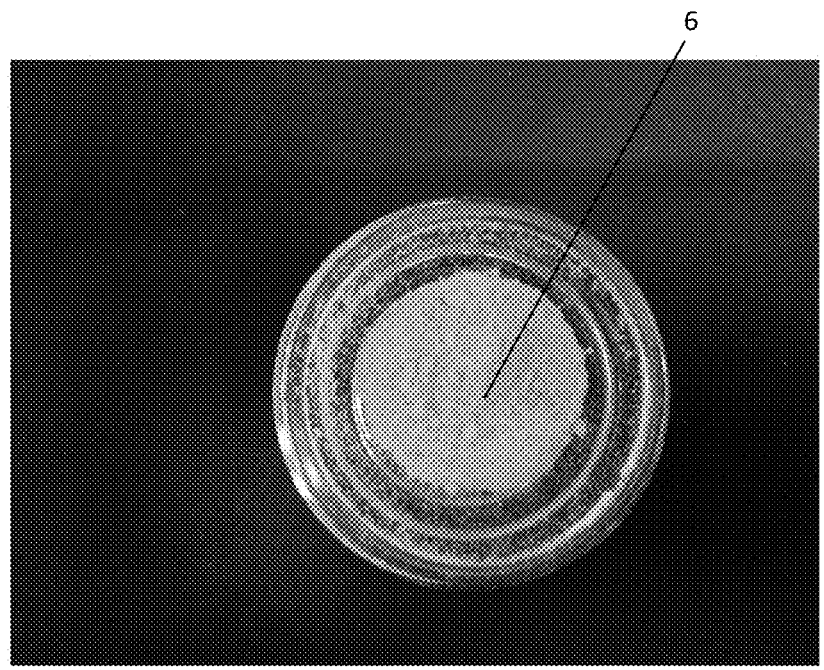
FIG. 3 is a photo of freeze dried disc material micronized to a fine powder.
Figure 4:
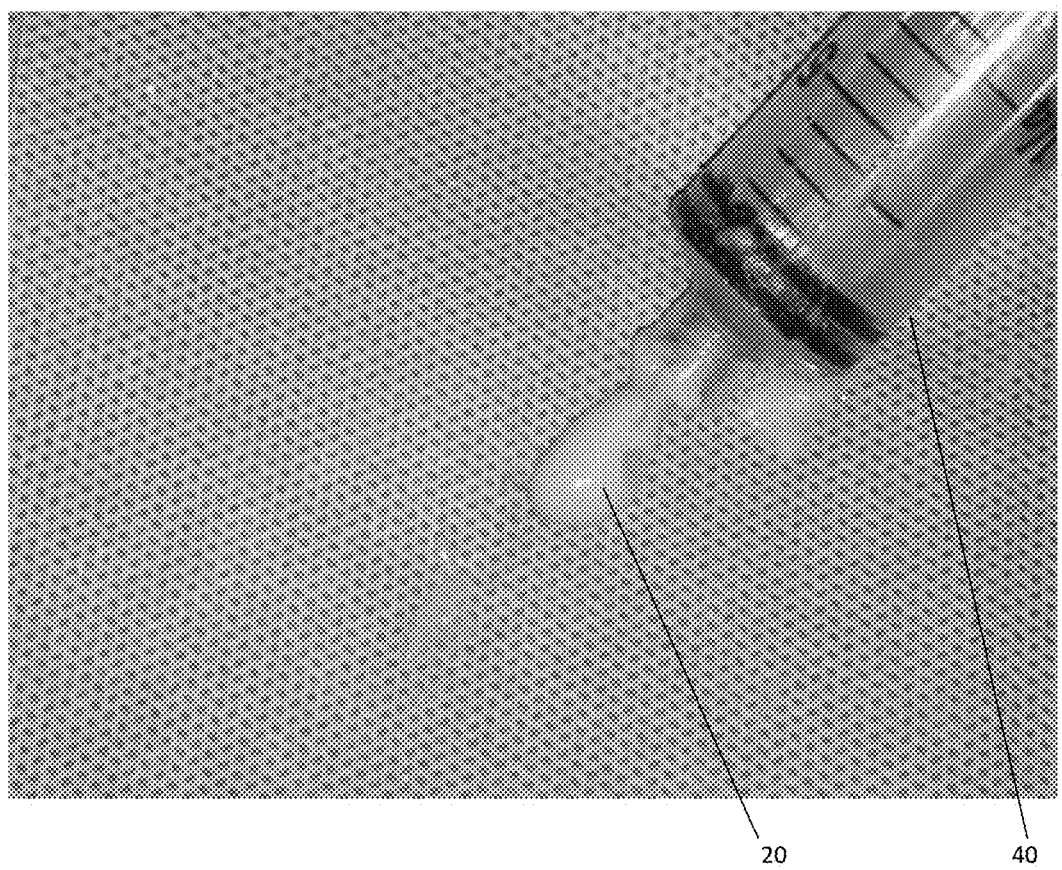
FIG. 4 is a photo showing the rehydrated disc material flowing from a syringe.

The actual disc material 6 is a recovered aseptically, preferably, from human cadaver spine segments 2 from approximately T9 to L5 as shown in FIG. 1A. These are done under sterile conditions. The spinal segments are immediately transferred to a processing room where the disc is isolated by cutting the junction between the end plate and the cancellous bone maintaining intact endplates of the vertebral body 4 above and below so as not to cause extrusion of the disc material as shown in FIG. 1B. The endplates are then removed and the nucleus pulposus is extracted using sharp dissection. The nucleus pulposus is then aggregated from all of the intervertebral discs for that particular case and are placed in a freeze drier and or cold desiccator where the moisture is removed to under 5 percent. The freeze dried material is then placed in aggregate into a cryomill 100 and micronized into a very fine powder 10 as shown in FIG. 2. Preferably, the mill 100 pulverizes the freeze dried nucleus pulposus at low temperatures not exceeding 40° C. to prevent material degradation. The micronized material has particles sized less than 400 microns. This fine powder 10, as shown in FIGS. 3 and 4, is then placed into a sterile container and can be stored under vacuum seal for long periods of time at room air. Once the fine powder material 10 is selected for administration, it is rehydrated using either normal saline, lactated ringers solution, blood, platelet rich plasma, or a combination of the above. It is then injected into the disc space using a 2-4 mm cannula, the smaller the cannula the better to prevent extrusion of the material out of the disc space following administration. Any pre-existing cracks or fissures are then sealed with fibrin glue after administration of the composite material.

The inventor has developed a biochamber whereby a human disc can be placed in a physiologic environment and loaded biomechanically. Simultaneously, various parameters can be continuously measured such as cellular activity, oxygen tension and glucose depletion.

It is believed a degenerative disc can be recovered and placed in a biological incubator and injected with the rehydrated freeze dried nucleus pulposus powder and incubated over a period of time to demonstrate physiologic repair and healing of the disc by increased metabolic activity, water retention and improved biomechanical strength.

This exemplary test protocol can be used to confirm the efficacy of the various reconstituted rehydrated mixtures proposed herein.

This allows for a unique method of preparing the material composition of proteoglycan containing nucleus pulposus comprising the steps of: Aseptic recovery of cadaveric spine segments 2, 4 from T9 to L5 (FIGS. 1A and 1B); Removal of the discs 6 by cutting between the cancellous bone and vertebral endplate junction; Removing the normal nucleus pulposus; Freeze drying the nucleus pulposus from multiple disc segments; Placing the freeze dried material into a cryomill 100 (FIG. 2); Placing the micronized disc material 10 into a sterile container for later use (FIG. 3).

Additionally, a test procedure may be used to confirm viability of the material which includes the step of: mixing the micronized disc material 10 with saline, stem cells, micronized amnion, platelet rich plasma, growth factors, PAMS (pharmacologically active microspheres), genetically altered cells that produce glycosaminoglycans. This rehydrated mixture 20 can be made a flowable material suitable for delivery from a nozzle type container such as a syringe. Once this micronized powder 10 is rehydrated it can be delivered to treat damaged or degenerative disc repair.

The treatment method can include the steps of: injecting the matrix composite through a 2-4 mm cannula into the disc space (FIG. 4). Smaller apertures through which this material may be injected may be preferable to limit extrusion of the material out of the disc space.

The spinal disc tissue can be prepared by dehydration at hypothermic temperatures.

Optionally, the disc material could be extracted from spine segments of primates or other mammals.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method for regenerating damaged spinal disc, the method consisting of:
   (a) obtaining from a human cadaver a normal intervertebral disc by sharp dissection;
   (b) removing the nucleus pulposus from the annulus fibrosis of the normal intervertebral disc;
   (c) hypothermically drying the nucleus pulposus to a moisture content of under 5 percent to form a dried material;
   (d) micronizing the dried material at a low temperature by placing the dried material in a cryomill and pulverizing the dried material to form particles sized less than 400 microns to form a micronized material;
   (e) placing the micronized material in a container for injection or in a syringe;
   (f) aseptically hydrating the micronized material by adding a fluid to the container for injection or to the syringe, such that the hydrated micronized material has a high but flowable viscosity which is flowable as an injectable through a small bore cannula; and
   (g) injecting the hydrated micronized material through a cannula into the damaged disc space, thereby regenerating the damaged disc.

2. The method of claim 1 wherein the treated disc regenerates or heals as evidenced by an increase in proteoglycans molecules.

3. A method for regenerating damaged spinal disc, the method consisting of:
   (a) obtaining from a human cadaver a normal intervertebral disc by sharp dissection;
   (b) removing the nucleus pulposus from the annulus fibrosis of the normal intervertebral disc.
   (c) hypothermically drying the nucleus pulposus to a moisture content of under 5 percent to form a dried material;
   (d) micronizing the dried material at a low temperature by placing the dried material in a cryomill and pulverizing the dried material to form particles sized less than 400 microns to form a micronized material;
   (e) placing the micronized material in a container for injection or in a syringe;
   (f) aseptically hydrating the micronized material by adding a fluid to the container for injection or to the syringe, such that the hydrated micronized material has a high but flowable viscosity which is flowable as an injectable through a small bore cannula;
   (g) injecting the hydrated micronized material through a cannula into the damaged disc space, thereby regenerating the damaged disc; and
   (h) sealing cracks in the damaged spinal disc with fibrin glue or other blood product to prevent leakage of the hydrated micronized material.

4. A method for regenerating damaged spinal disc, the method consisting of:
   (a) obtaining from a human cadaver a normal intervertebral disc by sharp dissection;
   (b) removing the nucleus pulposus from the annulus fibrosis of the normal intervertebral disc;
   (c) hypothermically drying the nucleus pulposus to a moisture content of under 5 percent to form a dried material;
   (d) micronizing the dried material at a low temperature by placing the dried material in a cryomill and pulverizing the dried material to form particles sized less than 400 microns to form a micronized material;
   (e) placing the micronized material in a container for injection or in a syringe;
   (f) aseptically hydrating the micronized material by adding a fluid to the container for injection or to the syringe, such that the hydrated micronized material has a high but flowable viscosity which is flowable as an injectable through a small bore cannula;
   (g) injecting the hydrated micronized material through a cannula sized 2 mm or less into the damaged disc space, thereby regenerating the damaged disc; and
   (h) sealing the hole in the damaged spinal disc with fibrin glue or another blood product.

5. A method for regenerating damaged spinal disc, the method consisting of:
   (a) obtaining from a human cadaver a normal intervertebral disc by sharp dissection;
   (b) removing the nucleus pulposus from the annulus fibrosis of the normal intervertebral disc;
   (c) hypothermically drying the nucleus pulposus to a moisture content of under 5 percent to form a dried material;
   (d) micronizing the dried material at a low temperature by placing the dried material in a cryomill and pulverizing the dried material to form particles sized less than 400 microns to form a micronized material;
   (e) placing the micronized material in a container for injection or in a syringe;
   (f) aseptically hydrating the micronized material by adding a fluid selected from the group consisting of normal saline, lactated ringers solution, blood, platelet rich plasma, or a combination thereof, and wherein the hydrated micronized material is a flowable mixture to the container for injection or to the syringe, such that the hydrated micronized material has a high but flowable viscosity which is flowable as an injectable through a small bore cannula;
   (g) mixing the flowable mixture with one or more of stem cells that are derived from marrow, fat, blood or interspinous ligaments; micronized amnion; collagen Type 1 or glucose; and (h) injecting the hydrated micronized material through a cannula into the damaged disc space, thereby regenerating the damaged disc.

* * * * *